(12) United States Patent
Astley et al.

(10) Patent No.: US 8,041,003 B2
(45) Date of Patent: Oct. 18, 2011

(54) ELECTRONIC PACKAGING TECHNIQUE TO IMPROVE SENSOR FAILURE ROBUSTNESS

(75) Inventors: Oliver Richard Astley, Niskayuna, NY (US); Naveen Chandra, Kenosha, WI (US); James Rose, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 129 days.

(21) Appl. No.: 12/551,355

(22) Filed: Aug. 31, 2009

(65) Prior Publication Data
US 2011/0051888 A1    Mar. 3, 2011

(51) Int. Cl.
  *H05G 1/60*    (2006.01)
(52) U.S. Cl. .......................................... 378/19
(58) Field of Classification Search ............. 378/19, 378/116
See application file for complete search history.

(56) References Cited

U.S. PATENT DOCUMENTS

| | | | |
|---|---|---|---|
| 6,995,581 B2 | 2/2006 | Barr et al. | |
| 7,286,068 B2 | 10/2007 | Stanley et al. | |
| 7,289,336 B2 | 10/2007 | Burdick, Jr. et al. | |
| 7,362,250 B2 | 4/2008 | Weibiao et al. | |
| 7,433,192 B2 | 10/2008 | Bambridge et al. | |
| 7,451,651 B2 * | 11/2008 | Woychik et al. ................ | 73/641 |

* cited by examiner

*Primary Examiner* — Jurie Yun
(74) *Attorney, Agent, or Firm* — Jason K. Klindtworth (57) ABSTRACT

A modular sensor assembly comprises: sensor arrays electrically coupled to a sensor substrate; a plurality of integrated circuits with sensor signal processors electrically coupled to a package substrate; and an interconnect assembly including electrical paths configured to electrically couple analog output signals from a first sensor array to a first integrated circuit and from a second sensor to a second integrated circuit, the first sensor disposed adjacent to the second sensor.

20 Claims, 9 Drawing Sheets

ELECTRONIC PACKAGING TECHNIQUE TO IMPROVE SENSOR FAILURE ROBUSTNESS

BACKGROUND OF THE INVENTION

The subject matter disclosed herein relates to modular sensor assemblies and, more particularly, to electronic packaging techniques for improving imaging sensor failure robustness.

Imaging sensor components, such as found in a computed tomography (CT) imaging system, for example, may utilize an x-ray source and x-ray detectors to scan a patient or other target. The x-ray detector typically includes an array of x-ray sensors used to read signals from the x-ray source. The image data obtained via the x-ray detectors may subsequently be used to construct cross-sectional images of the patient from the scanning operation.

Figure 1:
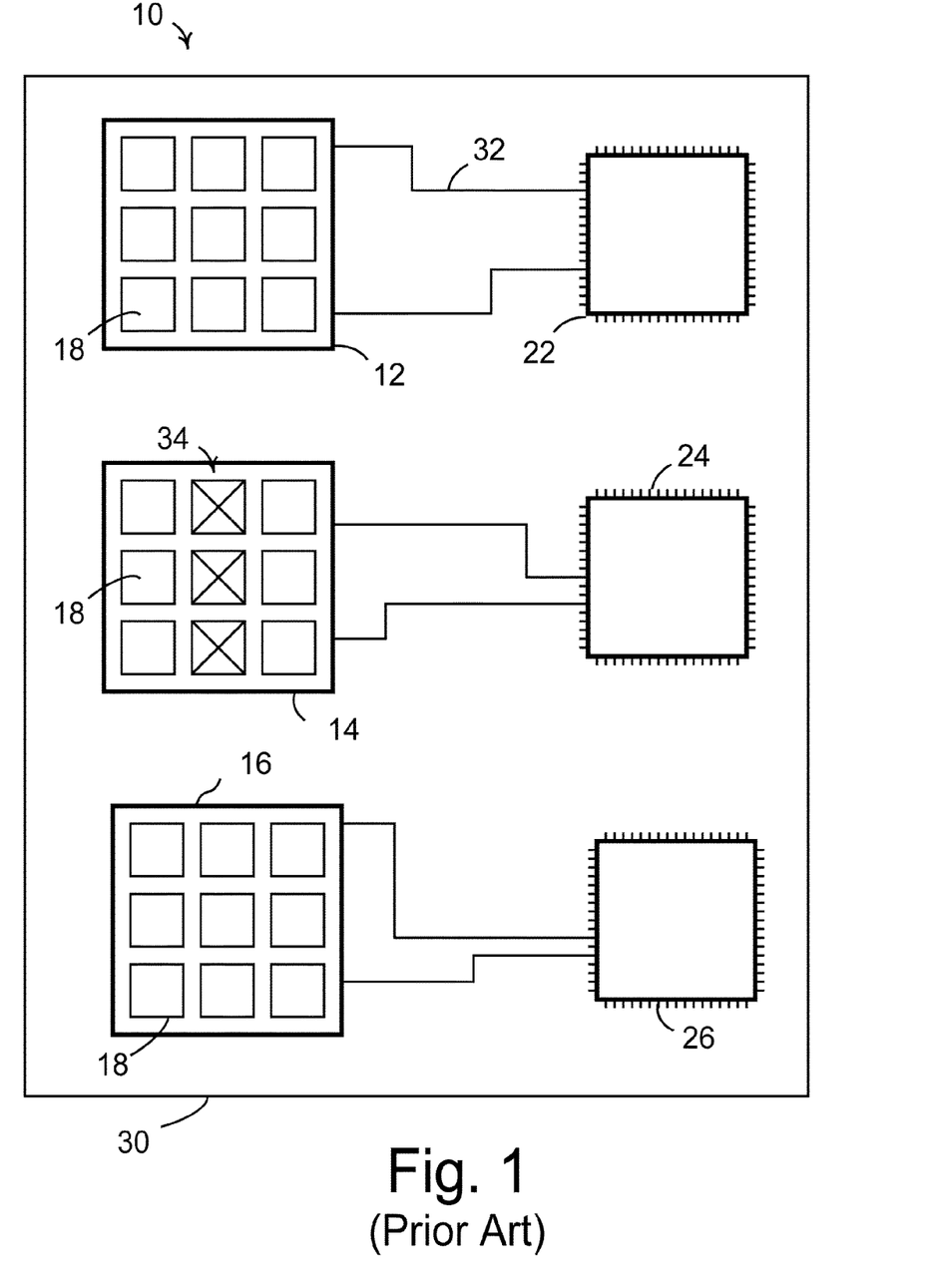
FIG. 1 shows a an x-ray detector comprising a plurality of x-ray sensor arrays and a plurality of integrated circuits, in accordance with the prior art.

As shown diagrammatically in FIG. 1, an x-ray detector 10 may comprise a plurality of x-ray sensors 18 grouped into x-ray sensor arrays 12, 14, and 16. Each x-ray sensor 18 may output an imaging signal, such as analog signal 32, to a respective analog-to-digital converter (ADC) for conversion to a digital signal, where the ADC may be fabricated as part of an integrated circuit (IC), such as IC 22, IC 24, and IC 26. As a single IC die may provide a plurality of analog-to-digital channels, the CT imaging system may thus include thousands of ICs to provide tens of thousands of sensor channels. As can be appreciated, the large number of ICs increases the probability that a random channel, such as channel 34, may fail, or that one of the ICs may fail.

Should a single channel of an IC fail, or an entire IC fail, there is little potential for recovery and/or correction without a better hardware design than shown in FIG. 1. What is needed is a sensor array capable of providing some recovery and/or correction when an imaging channel or an integrated circuit fails.

BRIEF DESCRIPTION OF THE INVENTION

In one aspect of the present invention, a modular sensor assembly comprises: one or more sensor arrays electrically coupled to a sensor substrate; a plurality of integrated circuits electrically coupled to a package substrate, each integrated circuit including a plurality of sensor signal processing components; and an interconnect assembly including a first electrical path configured to electrically couple an analog output signal from a first sensor in a first sensor array to a first integrated circuit, and a second electrical path configured to electrically couple an analog output signal from a second sensor to a second integrated circuit, the first sensor disposed adjacent to the second sensor.

In another aspect of the present invention, an imaging sensor assembly comprises: a plurality of imaging sensor arrays electrically coupled to a sensor substrate, each imaging sensor array including a two-dimensional array of imaging sensors responsive to x-ray radiation; a plurality of integrated circuits electrically coupled to a package substrate, each integrated circuit including a plurality of sensor signal processing components; and an interconnect assembly electrically coupled to the sensor substrate and to the package substrate, the interconnect assembly including a plurality of electrical paths configured to electrically couple analog output signals from one of the imaging sensor arrays to two or more of the integrated circuits.

In yet another aspect of the present invention, a computed tomography imaging system comprises: an x-ray source disposed in a gantry; a detector assembly for receiving an x-ray emission from the x-ray source, the x-ray source and the detector assembly rotatable about the imaging target, the detector including: a plurality of imaging sensor arrays electrically coupled to a sensor substrate; a plurality of integrated circuits electrically coupled to a package substrate; an interconnect assembly electrically coupled to the sensor substrate and to the package substrate, the interconnect assembly including a plurality of electrical paths configured to electrically couple analog output signals from one of the imaging sensor arrays to two or more of the integrated circuits; an imager control system for selectively modulating the x-ray source during a scan slice; and a computer for receiving data from the detector assembly.

Other devices and/or methods according to the disclosed embodiments will become or are apparent to one with skill in the art upon review of the following drawings and detailed description. It is intended that all such additional devices and methods are within the scope of the present invention, and are protected by the accompanying claims.

DETAILED DESCRIPTION OF THE INVENTION

The present invention includes a method to implement interleaving in a modular sensor assembly incorporating a plurality of application specific integrated circuit (ASIC) dies, wherein imaging sensors are connected to the ASIC dies in an interleaved configuration for fault tolerance, and multiple power connections may be provided to the ASIC dies for redundancy. The disclosed configuration allows for the ASIC dies to be emplaced in a single physical package along with the fault tolerant interconnect configuration. In the event of channel failure or ASIC failure, the interleaving feature enables recovery, thus allowing a user to continue imaging and reduce "system downtime."

Figure 2:
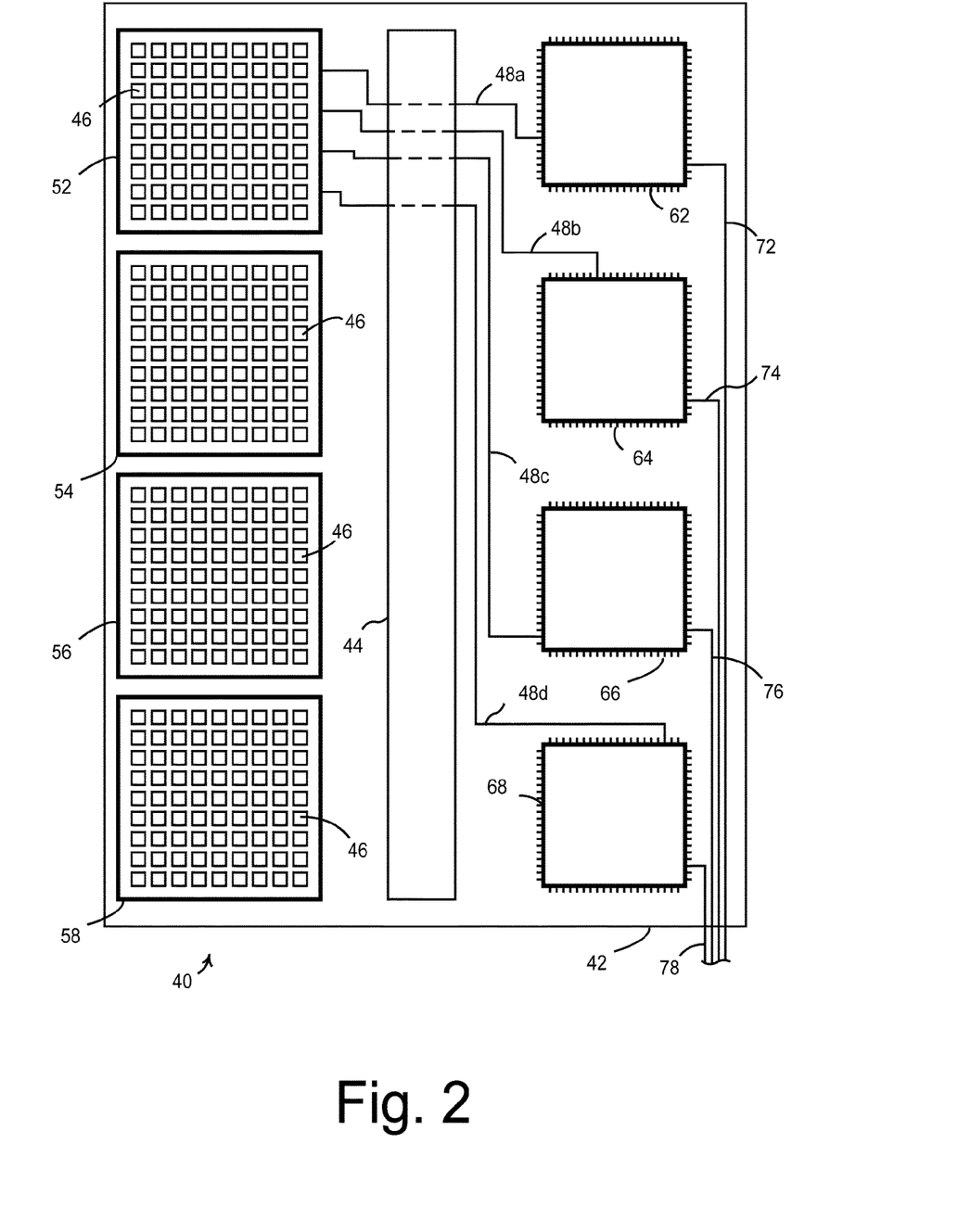
FIG. 2 is a diagrammatical illustration of a modular sensor assembly comprising multiple sensor arrays and multiple application-specific integrated circuit dies, in accordance with an aspect of the invention.

FIG. 2 is a diagrammatical illustration of an exemplary embodiment of a modular sensor assembly comprising one or more sensor arrays and multiple ASIC dies, in accordance with an aspect of the invention. In the particular configuration shown, a modular sensor assembly 40 comprises four sensor arrays 52, 54, 56, and 58 connected to four ASIC dies 62, 64, 66, and 68, by means of an interconnect component 44, described in greater detail below. Each sensor array 52, 54, 56, and 58 includes a plurality of sensors 46, shown here as configured in two-dimensional x-z arrays, although a one-dimensional array of sensors may be used. Each sensor 46 is responsive to incident radiation energy, such as x-ray radiation, to output an analog signal to a respective sensor signal processing component (not shown), in one of the ASIC dies 62, 64, 66, and 68 for conversion to a digital signal, as explained in greater detail below. That is, there is provided a signal processing device in one of the ASIC dies 62, 64, 66, and 68 for each of a corresponding imaging sensor 46 in one of the sensor arrays 52, 54, 56, and 58. In an exemplary embodiment, the signal processing component may comprise an analog-to-digital converter (ADC) in the ASIC die, or a preamplifier in the ASIC die in electrical communication with a corresponding ADC in a remote circuit (not shown).

The interleaving configuration of the modular sensor assembly 40 can be seen with reference to the interconnection configurations provided between the sensor arrays 52, 54, 56, and 58 and the ASIC dies 62, 64, 66, and 68. As shown in the illustration, the sensor array 52 includes at least one sensor 46 that provides an output signal to an ADC or a preamplifier in the first ASIC die 62 via an electrical path 48a. The sensor array 52 further includes at least three additional sensors 46, where each of the three additional sensors 46 provides an output signal to: (i) one of a preamplifier or an analog-to-digital converter in the second ASIC die 64 via an electrical path 48b, (ii) an analog-to-digital converter or a preamplifier in the third ASIC die 66 via an electrical path 48c, or (iii) an analog-to-digital converter or preamplifier in the fourth ASIC die 68 via an electrical path 48d. The analog sensor signals from the sensor array 52 is thus provided to respective ADCs or preamplifiers in four separate ASIC dies. In general, analog sensor signals from a single sensor array are provided to multiple sensor signal processing components in two or more ASIC dies for conversion to digital signals to provide for the fault tolerant interconnect configuration. This interleaved configuration serves to mitigate or eliminate imaging problems that can result from failures in the sensor arrays and failures in the ASIC dies, as described in greater detail below.

In similar configurations: (i) each of the sensors 46 in the sensor array 54 is electrically connected to a respective sensor signal processing component (not shown) in one of the ASICs 62, 64, 66, and 68; (ii) each of the sensors 46 in the sensor array 56 is electrically connected to a respective sensor signal processing component in one of the ASICs 62, 64, 66, and 68; and (iii) each of the sensors 46 in the sensor array 58 is electrically connected to a respective sensor signal processing component in one of the ASICs 62, 64, 66, and 68. It should be understood that, while only the four electrical paths 48a, 48b, 48c, and 48d are shown for clarity of illustration, an electrical path is provided via the interconnect assembly 44 in the modular sensor assembly 40 between each of the sensors 46 in each of the four sensor arrays 52, 54, 56, and 58 and a respective sensor signal processing component in the ASIC dies 62, 64, 66, and 68.

In an alternative exemplary embodiment, individual power lines may be provided to the ASIC dies for power redundancy. In the configuration shown, an individual power line 72 may be provided to the ASIC die 62 only. If the ASIC die 62 incurs a fault that causes an interruption of power on the power line 72, for example, a second, separate power line 74 will continue to provide power to the ASIC die 64, a third power line 76 will continue to provide power to the ASIC die 66, and a fourth power line 78 will continue to provide power to the ASIC die 68.

Figure 3:
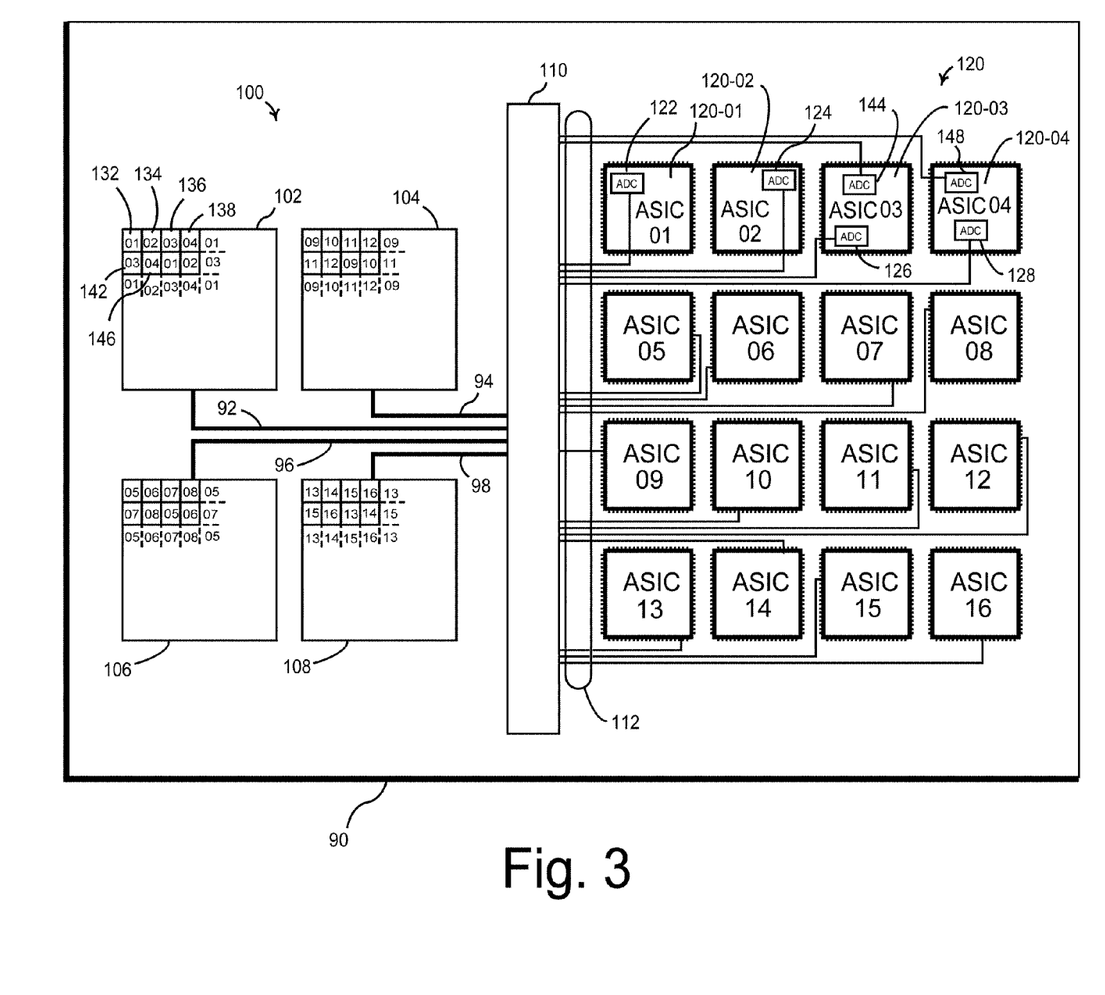
FIG. 3 is a diagrammatical illustration of an interleaving interconnection configuration for a modular sensor assembly comprising a plurality of sensor arrays and a plurality of application-specific integrated circuit dies, in accordance with an exemplary aspect of the invention.

FIG. 3 is a diagrammatical illustration of an exemplary interleaving interconnection configuration for a modular sensor assembly 90 comprising a plurality of sensor arrays and a plurality of ASIC dies, in accordance with an aspect of the invention. A sensor array 100 is shown here presented as a first sensor array quadrant 102, a second sensor array quadrant 104, a third sensor array quadrant 106, and a fourth sensor array quadrant 108. It should be understood that this physical partitioning of the sensor array 100 into four sensor array quadrants is optional and that, depending on design requirements or fabrication preferences, the sensor array 100 may be partitioned into another physical arrangement, or may comprise a unitary array of imaging sensors. Moreover, as the modular sensor assemblies disclosed herein may be used in different applications for different radiation detection applications, the physical arrangement of the sensor arrays may be specified for optimal detection of the incident radiation.

The sensor array 100 provides multiple analog sensor signals to an integrated circuit die array 120, here shown comprising integrated circuit components denoted as ASIC 01 through ASIC 16. The first sensor array quadrant 102 may provide analog signals via an analog bus 92 to a first group of four integrated circuits, such as the die 120-01 (ASIC 01), the die 120-02 (ASIC 02), the die 120-03 (ASIC 03), and the die 120-04 (ASIC 04). Accordingly, the analog bus 92 includes an electrical path for each of the imaging sensors in the first sensor array quadrant 102. In an exemplary embodiment, each sensor array quadrant may comprise a plurality of imaging sensors arranged in eight columns (x-direction) and thirty-two rows (z-direction) for a total of 256 imaging sensors.

Similarly, the second sensor array quadrant 104 may provide analog sensor signals via an analog bus 94 to a second group of integrated circuits, here shown as ASIC 05 through ASIC 08. The third sensor array quadrant 106 may provide analog sensor signals via an analog bus 96 to a third group of integrated circuits comprising ASIC 09 through ASIC 12, and the fourth sensor array quadrant 108 may provide analog sensor signals via an analog bus 98 to a fourth group of integrated circuits comprising ASIC 13 through ASIC 16. The electrical paths originating in the four sensor array quadrants shown are mapped, via an inter-digitated conductive pattern (not shown) in an interconnect assembly 110, into a plurality of output electrical paths, denoted here as interconnect output 112.

In an exemplary embodiment, an imaging sensor 132, labeled in the illustration with the designation "01" and located in the first column and the first row of the first sensor array quadrant 102, is electrically connected to an ADC 122 in the die 120-01. It should be understood that, while ADCs are shown in the ASIC array 120, other sensor signal processing components can be used as well, such as preamplifiers connected to remote analog-to-digital converters, in accordance with an aspect of the invention. Similarly, an imaging sensor 134, labeled as "02" and located in the second column and first row of the first sensor array quadrant 102, is electrically connected to an ADC 124 in the die 120-02. An imaging sensor 136, labeled as "03" and located in the third column and first row of the first sensor array quadrant 102, is electrically connected to an ADC 126 in the die 120-03, and an imaging sensor 138, labeled as "04" and located in the fourth column and first row of the first sensor array quadrant 102, is electrically connected to an ADC 128 in the die 120-04. This pattern may be repeated in the remainder of the first row, with an imaging sensor labeled as "01" and located in the fifth column, for example, electrically connected to a sensor signal processing component in the die 120-01, and so on as represented by the numbered designations "01" through "04."

In the second row of the first sensor array quadrant 102, an imaging sensor 142 in the first column is electrically connected to an ADC 144 in the die 120-03 and an imaging sensor 146 in the second column is electrically connected to an ADC 148 in the die 120-04. The interconnect pattern "01" through "04" repeats beginning with the next sensor in the second row being electrically connected to the die 120-01, as shown in the partial array of imaging sensors in the first sensor array quadrant 102. The pattern for the third row is similar to the pattern for the first row. Generally, each imaging sensor labeled as "01" is electrically connected to a respective ADC in ASIC 01, each imaging sensor labeled as "02" is electrically connected to a respective ADC in ASIC 02, each imaging sensor labeled as "03" is electrically connected to a respective ADC in ASIC 03, and each imaging sensor labeled as "04" is electrically connected to a respective ADC in ASIC 04.

An imaging sensor labeled as "09" and located in the first column and the first row of the second sensor array quadrant 104, is electrically connected to an ADC in ASIC 09. An imaging sensor labeled as "10" and located in the second column and first row is electrically connected to an ADC in ASIC 10, an imaging sensor labeled as "11" and located in the third column and first row is electrically connected to an ADC in ASIC 11, and an imaging sensor labeled as "12" and located in the fourth column is electrically connected to an ADC in ASIC 12. That is, the interconnect pattern in the second sensor array quadrant 104 follows the interconnect pattern in the first sensor array quadrant, such that adjacent rows are offset by two imaging sensors. Accordingly, each imaging sensor labeled as "09" in the second sensor array quadrant 104 is electrically connected to a respective ADC in ASIC 09, each imaging sensor labeled as "10" is electrically connected to a respective ADC in ASIC 10, each imaging sensor labeled as "11" is electrically connected to a respective ADC in ASIC 11, and each imaging sensor labeled as "12" is electrically connected to a respective ADC in ASIC 12.

The above interconnection pattern is similar from the third sensor array quadrant 106 to respective ADCs in ASIC 05 through ASIC 08, and from the fourth sensor array quadrant 108 to respective ADCs in ASIC 13 through ASIC 16. In the third sensor array quadrant 106, for example, imaging sensors "05" in the first column, first row and in the third column second row are electrically connected to respective ADCs in ASIC 05; imaging sensors "06" in the second column, first row and in the fourth column second row are electrically connected to respective ADCs in ASIC 06; imaging sensors "07" in the third column, first row and in the first column second row are electrically connected to respective ADCs in ASIC 07; and imaging sensors "08" in the fourth column, first row and in the second column second row are electrically connected to respective ADCs in ASIC 07. Generally for each of the sensor array quadrants, a first analog output is provided from a first sensor to a first ASIC, and a second analog output is provided from a second sensor to a second ASIC, where the first sensor is located adjacent to the second sensor.

Figure 4:
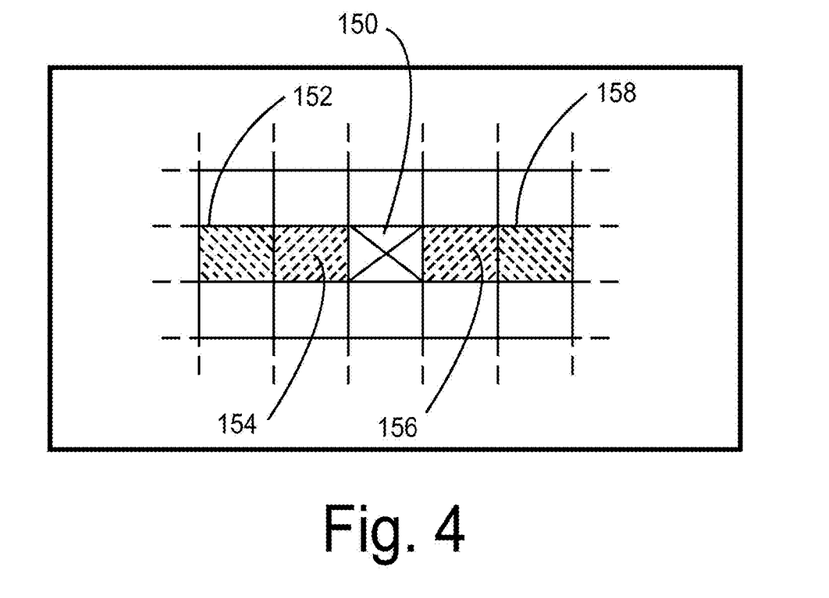
FIG. 4 is a diagram illustrating recovery and correction for a sensor shorted to ground.

The interconnection pattern disclosed in FIG. 3 may serve to provide recovery and/or correction to imaging data output from a modular sensor assembly when an imaging sensor 150 has failed (indicated by an "X") by shorting to ground and losing charge, for example, as shown in FIG. 4. Generally, in the event of a channel failure or the failure of an entire ASIC die, an external image processing subsystem (not shown) may function to ignore sensor data signals from the failed channel or ASIC die. Faulty analog signals from a problem channel may be detected by using the data from neighboring, unaffected sensors through the use of interpolation or other algorithmic means. It can be appreciated by one skilled in the art that the disclosed configuration serves to provide a reduced risk of contiguous sensor data, such as resulting from an ASIC failure, because the electrical connections and routing channels are interleaved among the plurality of ASIC dies. This serves to insure that signal data from neighboring sensors are made available, even if one of the ASIC dies has failed.

In the example shown, correction may be provided by means of a correction algorithm and the data obtained from two non-shorted sensors 152 and 154 in the adjacent columns to the left of the shorted sensor 150 (identified by hatch lines), and data obtained from two non-shorted sensors 156 and 158 in the adjacent columns to the right of the shorted sensor 150 (also identified by hatch lines). Accordingly, in an exemplary sensor array, any two sensors, denoted by "N-01" and "N-02," that are connected to the same ASIC, denoted by "N," are spaced in the x-direction with at least two columns of imaging sensors disposed between the sensor N-01 and the sensor N-02.

In an alternative exemplary configuration, the sensors in the first sensor array quadrant 102, shown in FIG. 3, may be connected to dies in both the first group of integrated circuits (ASIC 01 through ASIC 04) and the second group of integrated circuits (ASIC 05 through ASIC 08). Similarly, the sensors in the second sensor array quadrant 104 may also be connected to dies in both the first group and the second group of integrated circuits. As can be appreciated by one skilled in the art, various signal routing configurations may be realized in the modular sensor assembly 90, while meeting the requirement of providing at least two columns of sensors between the sensor N-01 and the sensor N-02.

Figure 5:
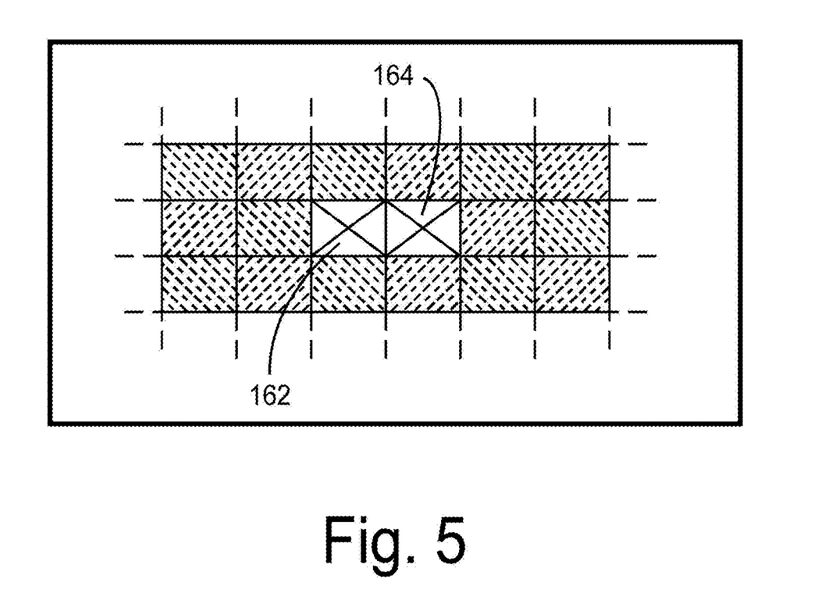
FIG. 5 is a diagram illustrating recovery and correction for a pair of sensors shorted to each other.

Recovery and/or correction may also be provided by an appropriate algorithm when a first sensor 162 has shorted to a second sensor 164, for example, as shown in FIG. 5. Correction may utilize (i) the data obtained from two non-shorted sensors in the adjacent columns to the left of the sensor 162, (ii) the data obtained from two non-shorted sensors in the adjacent columns to the right of the sensor 164, (iii) the data obtained from six sensors in the row above the row with the sensors 162 and 164, and (iv) the data obtained from six sensors in the row below the row with the sensors 162 and 164. Accordingly, in an exemplary sensor array, in the z-direction, the channels of the same ASIC die "N" are spaced with at least one sensor between a sensor N-03 and a sensor N-04.

Figure 6:
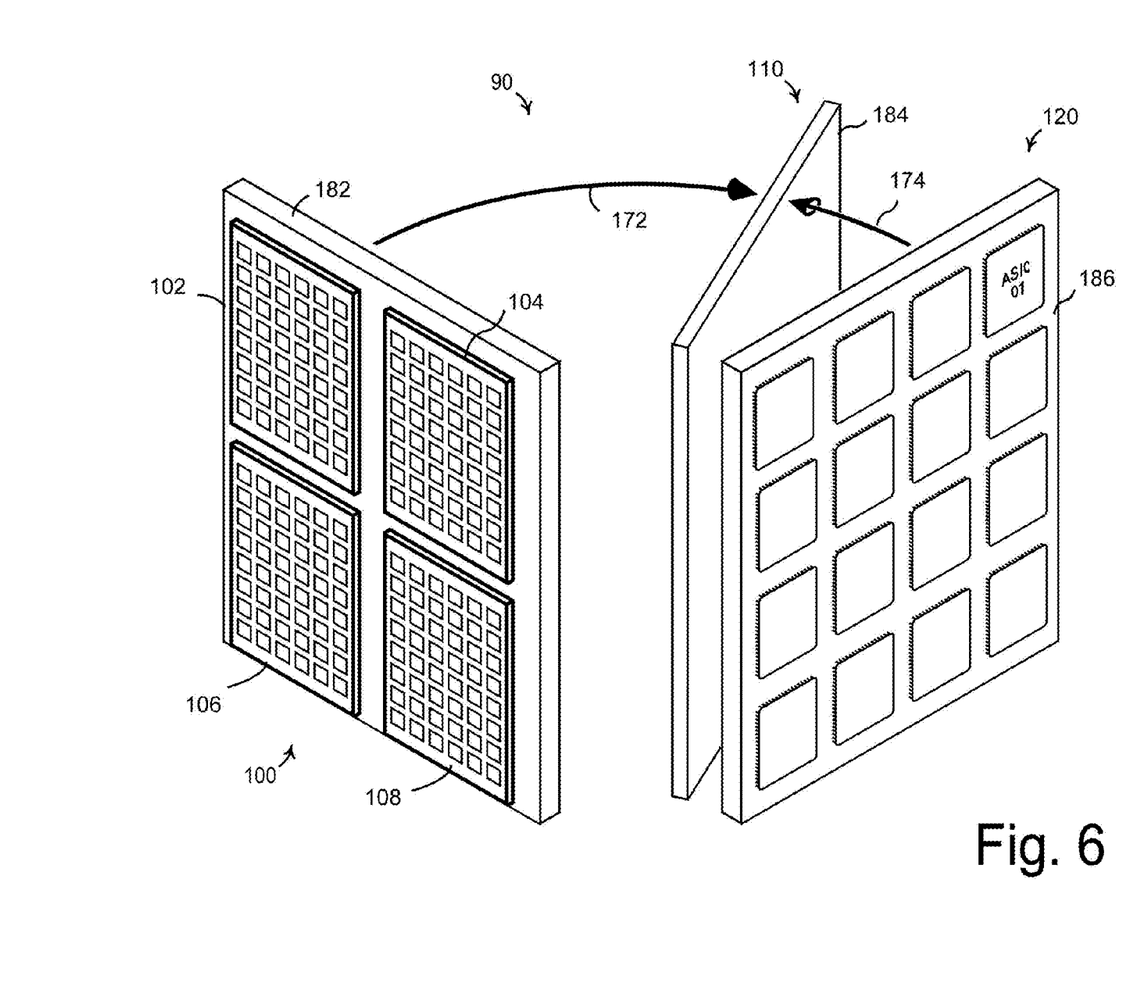
FIG. 6 is a diagrammatical isometric illustration of a modular sensor assembly comprising a sensor array on a sensor substrate, an integrated circuit group on a package substrate, and an interconnect assembly on an electrical substrate, in accordance with an aspect of the invention.

The modular sensor assembly 90, shown diagrammatically in FIG. 3, may be physically configured as shown in the isometric diagram of FIG. 6 in which the first sensor array quadrant 102, the second sensor array quadrant 104, the third sensor array quadrant 106, and the fourth sensor array quadrant 108 are disposed on a sensor substrate 182 to form the sensor array 100. ASIC 01 through ASIC 16, here shown as "flip chips," may be disposed on a package substrate 186 to form the ASIC group 120. An electrical substrate 184 may include electrical contacts on a first surface to mate with corresponding electrical contacts (not shown), such as gold-plated lands or solder balls, on the sensor substrate 182, and may include electrical contacts on a second surface to mate with electrical contacts (not shown) on the package substrate 186.

The electrical substrate 184 includes surface or internal electrical paths (not shown) corresponding to the analog buses 92, 94, 96 and 98, and the interconnect output 112, to form the interconnect assembly 110. The sensor substrate 182 may be positioned against, or deposited onto, the first surface of the electrical substrate 184 as indicated by arrow 172, and the package substrate 186 may be positioned against, or deposited onto, the second surface of the electrical substrate as indicated by arrow 174, to physically form the modular sensor assembly 90 using fabrication methods known in the relevant art.

Figure 7:
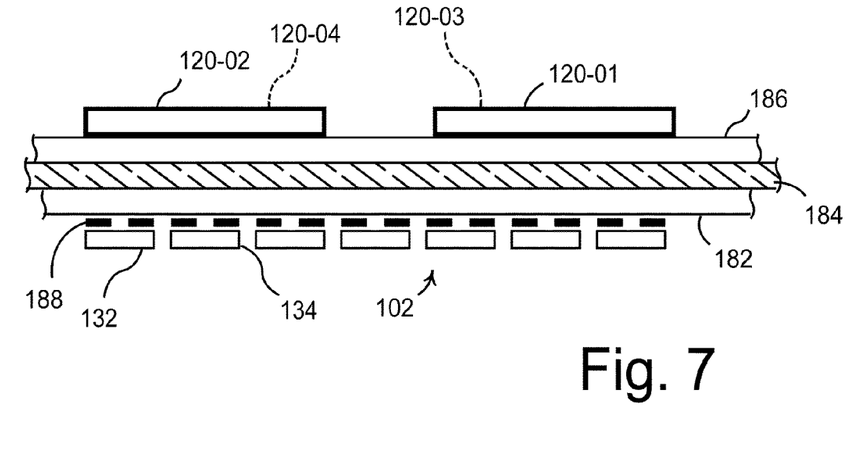
FIG. 7 is an end view of the modular sensor assembly of FIG. 6, showing a stack up of the sensor substrate, the electrical substrate, and the package substrate.

As shown in the end or elevation view of FIG. 7, a modular sensor assembly 190 may comprise a stack up of the sensor substrate 182, the electrical substrate 184, and the package substrate 186. The sensors, such as sensors 132 and 134, may be attached to the sensor substrate 182 using gold-plated lands 188, or solder balls on a printed circuit board (not shown), for example, to form the first sensor array quadrant 102. The package substrate 186 may also include the power lines 72-78 (not shown) of FIG. 2.

Figure 8:
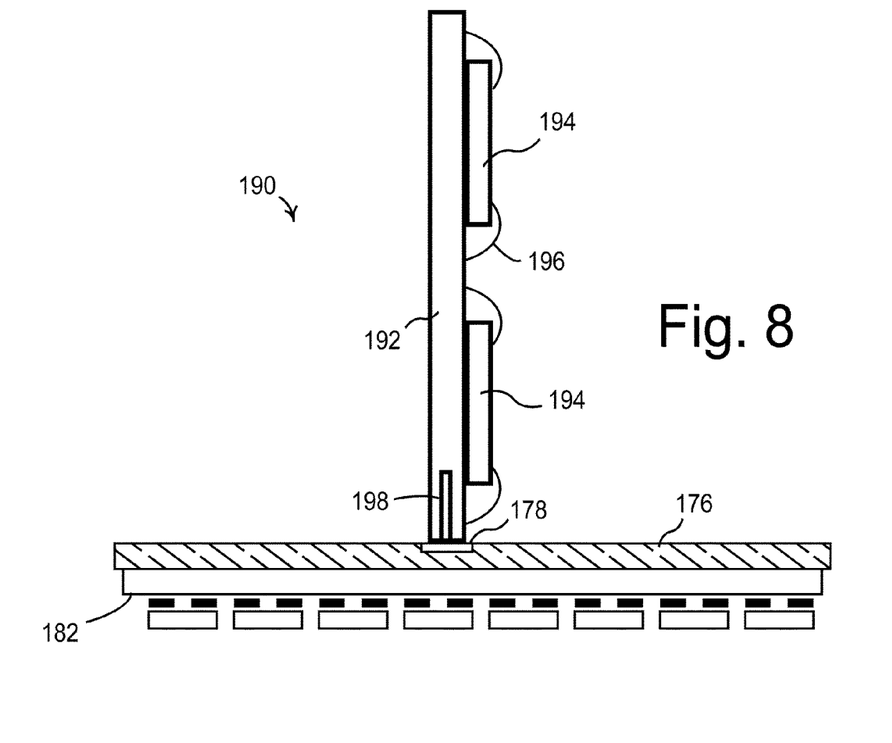
FIG. 8 is an alternative exemplary embodiment of the modular sensor assembly of FIG. 7 showing an alternate method of electrically connecting the package substrate.

In an alternative exemplary embodiment, a modular sensor assembly 190 may include a stack up of the sensor substrate 182 and an alternative electrical substrate 176, with an edge-mounted package substrate 192 comprising a plurality of edge input/output connectors 198 configured to mate with corresponding electrical contacts 178 on the electrical substrate 176. See, for example, commonly-assigned U.S. Pat. No. 6,990,176 "Methods and apparatus for tileable sensor array," incorporated herein in entirety by reference. The electrical substrate 192 may be configured to allow for attachment of ASIC dies 194 with wire bonds 196, as known in the art.

Figure 9:
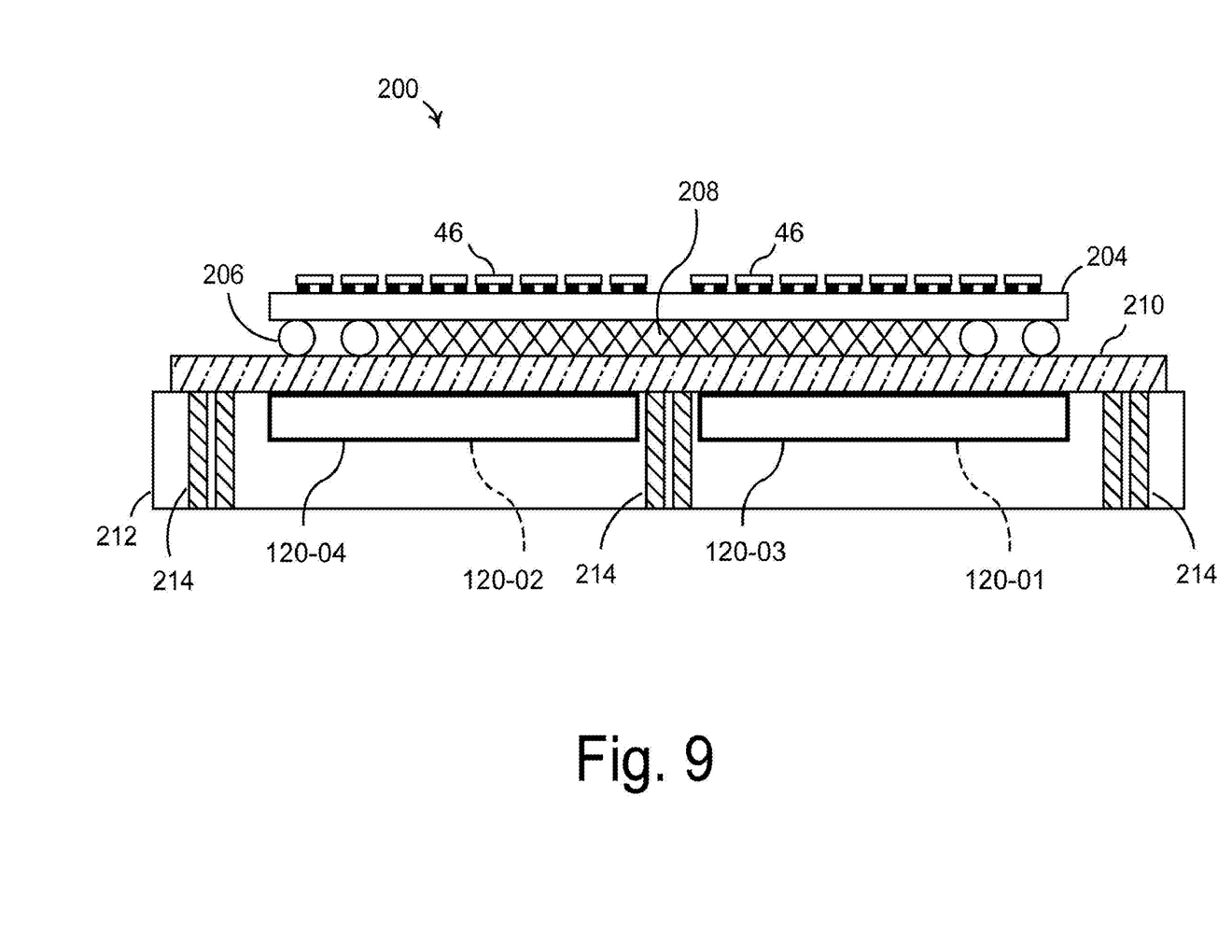
FIG. 9 is a diagrammatical illustration of an alternative embodiment of a modular sensor assembly showing a sensor array and an integrated circuit group mounted directly to an interconnect assembly.

In another exemplary embodiment, shown in FIG. 9, a modular sensor assembly 200 may comprise a package substrate 210, and a plurality of sensors 46 disposed on a sensor substrate 204. The package substrate 210 may be fabricated as a unitary component comprising the sensor substrate 182 and the electrical substrate 184 of FIG. 7. The sensor substrate 204 may be attached to one surface of the package substrate 210 by a plurality of solder balls 206 attached to gold-plated pads (not shown). An underfill 208, comprising a nonconductive epoxy for example, may be provided to ensure mechanical support of the sensor substrate 204.

Alternatively, the sensor substrate 204 may comprise an array of conductive epoxy "dots," or an array of aluminum pads (not shown), on a silicon substrate material, where gold "stud bumps" may be bonded to the aluminum pads. The package substrate 210 may also include electrical contacts (not shown) comprising gold-plated pads, to mate with the solder balls 206. See, for example, commonly-assigned U.S. Patent Application Publication 2008/0006773 "Electrical interface for a sensor array" incorporated herein in entirety by reference.

The package substrate 210 may further include surface or internal electrical paths (not shown) corresponding to one or more of the analog buses 92, 94, 96 and 98, and some or all of the interconnect output 112 (shown in FIG. 3). Accordingly, the die 120-01 (ASIC 01) and the die 120-02 (ASIC 02) may be attached to a second surface of the package substrate 210, as shown, forming a 2×2 array with the dies 120-03 and 120-04 (hidden from view in the illustration). The package substrate 210 may be attached to a support substrate 212 within which may be provided a plurality of conductive vias 214 for routing of electrical power and signals to external circuitry (not shown).

Figure 10:
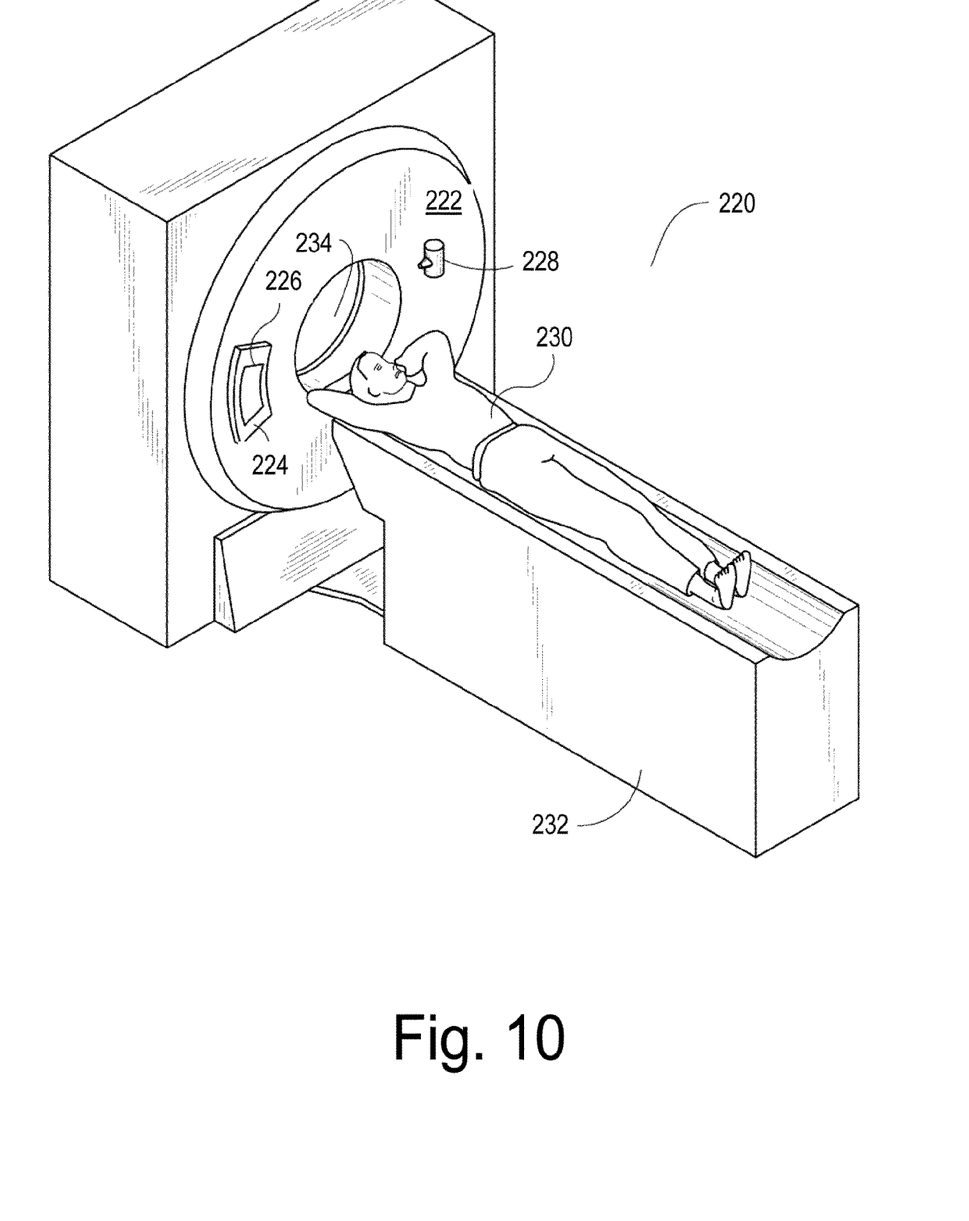
FIG. 10 is a diagrammatical isometric illustration of a computed tomography imaging system comprising a modular sensor assembly in a detector assembly, in accordance with one aspect of the invention.

The modular sensor assemblies 40, 90, 190, and 200 disclosed above may be used in various imaging systems including, for example, a "third generation" CT imaging system 220 shown in FIG. 10. The CT imaging system 220 comprises a gantry 222, with a collimator assembly 224, a data acquisition system 226, and an x-ray source 228 disposed on the gantry 222 as shown. A table 232 serves to move all or part of a patient 230 through a gantry opening 234 in the gantry 222. As shown in the functional block diagram of FIG. 11, the x-ray source 228 projects a beam of x-rays 240 through the patient 230 onto a detector assembly 250 comprising: (i) a one-dimensional or two-dimensional array of any of the modular sensor assemblies 40, 90, 190, and 200 configured for detection of x-ray radiation; (ii) the collimator assembly 224; and, (iii) the data acquisition system 226.

Figure 11:
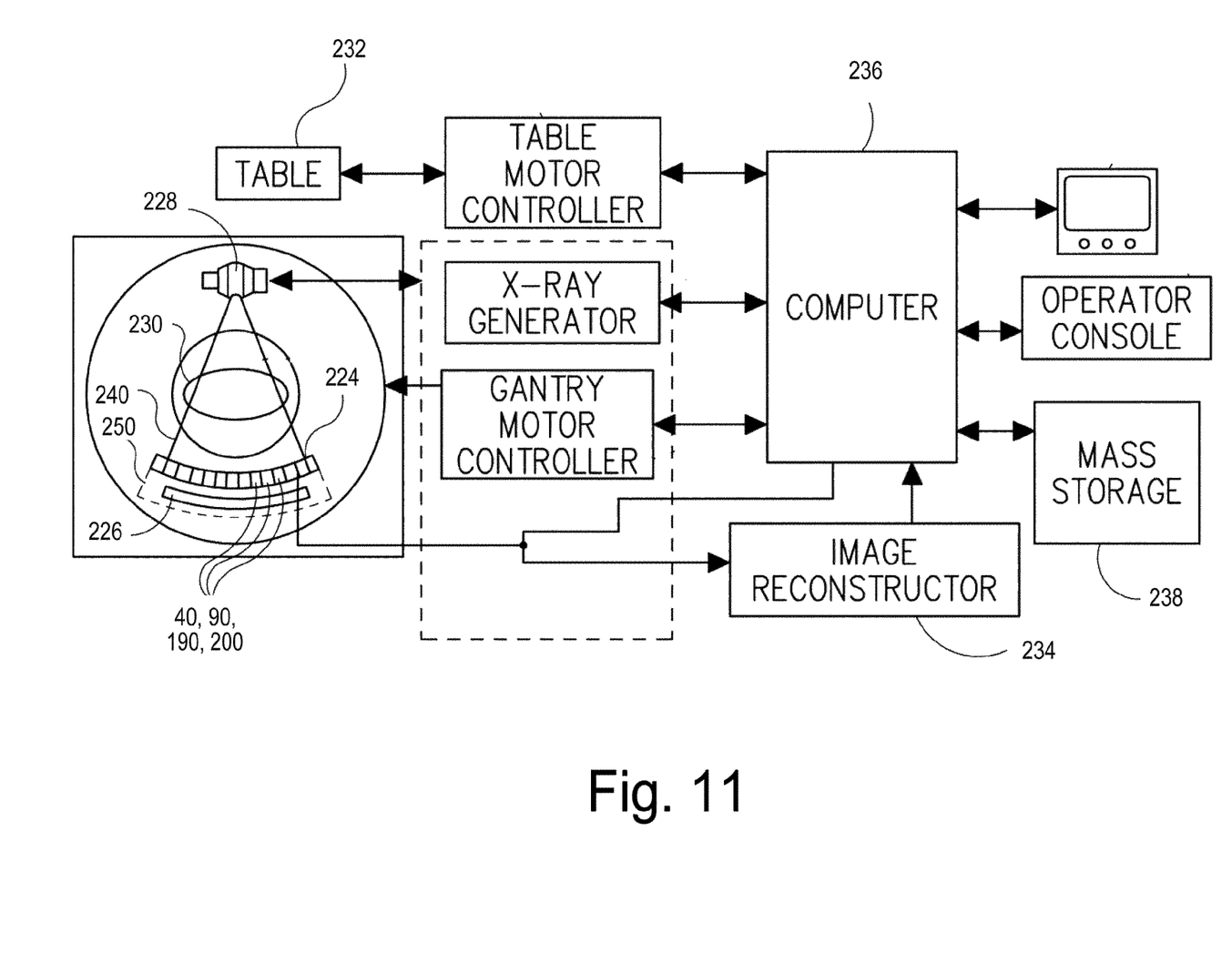
FIG. 11 is a functional diagram of the computed tomography imaging system of FIG. 10, showing the modular sensor assemblies of FIG. 2 and FIGS. 6-8 in the detector assembly.

The modular sensor assemblies 40, 90, 190, or 200 in the detector assembly 250 sense the projected x-rays that pass through the patient 230, and the data acquisition system 226 converts the ADC outputs to digital signals for subsequent processing. An image reconstructor 234 receives sampled and digitized x-ray data from the data acquisition system 226 and performs high speed reconstruction. The reconstructed image is applied as an input to a computer 236 which stores the image in a mass storage device 238.

While the present invention is described with reference to various exemplary embodiments, it will be understood by those skilled in the art that various changes may be made and equivalence may be substituted for elements thereof without departing from the scope of the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. In particular, certain modifications may be made to the teachings of the invention to adapt to a particular situation without departing from the scope thereof. Therefore, it is intended that the invention not be limited to the embodiments disclosed above for carrying out this invention, but that the invention include all embodiments falling with the scope of the intended claims.

What is claimed is:

1. A modular sensor assembly comprising:
    one or more sensor arrays electrically coupled to a first substrate;
    a plurality of integrated circuits electrically coupled to a second substrate, each said integrated circuit including a plurality of sensor signal processing components; and
    an interconnect assembly comprising:
        a first electrical path configured to electrically couple an analog output signal from a first sensor in a first sensor array to a first integrated circuit;
        a second electrical path configured to electrically couple an analog output signal from a second sensor to a second integrated circuit, said first sensor disposed adjacent to said second sensor; and
        a third electrical path configured to electrically couple an analog output signal from a third sensor in said first sensor array to said first integrated circuit, said second sensor disposed between said first sensor and said third sensor.

2. The modular sensor assembly of claim 1 further comprising a plurality of power lines, each said power line connected to a respective one of said integrated circuits.

3. The modular sensor assembly of claim 1 wherein said sensor signal processing components comprise one of a preamplifier and an analog-to-digital converter.

4. The modular sensor assembly of claim 1 wherein each said sensor array comprises one of a one-dimensional array of sensors and a two-dimensional array of sensors.

5. The modular sensor assembly of claim 4 wherein said interconnect assembly is configured to electrically connect: an analog output signal from a sensor in a first column and first row of said two dimensional array of sensors to said first integrated circuit, an analog output signal from a sensor in a second column and said first row to said second integrated circuit, and an analog output signal from a sensor in a third column and said first row to a third integrated circuit.

6. The modular sensor assembly of claim 5 wherein said interconnect assembly is further configured to electrically connect: an analog output signal from a sensor in a first column and second row of said two dimensional array of sensors to said third integrated circuit, an analog output signal from a sensor in a second column and said second row to a fourth integrated circuit, and an analog output signal from a sensor in a third column and said second row to said first integrated circuit.

7. The modular sensor assembly of claim 1 wherein said interconnect assembly comprises an electrical substrate disposed between said first substrate and said second substrate.

8. The modular sensor assembly of claim 1 wherein said second substrate comprises one of surface electrical paths and internal electrical paths to form said interconnect assembly.

9. A modular sensor assembly of claim 1 wherein said one or more sensor arrays comprises four sensor arrays connected to four ASIC dies.

10. An imaging sensor assembly comprising:
a plurality of imaging sensor arrays electrically coupled to a sensor substrate, each said imaging sensor array including a two-dimensional array of imaging sensors responsive to x-ray radiation, wherein said plurality of imaging sensor arrays includes four sensor array quadrants;
a plurality of integrated circuits electrically coupled to a package substrate, each said integrated circuit including a plurality of sensor signal processing components, wherein said plurality of integrated circuits includes sixteen integrated circuits; and
an interconnect assembly electrically coupled to said sensor substrate and to said package substrate, said interconnect assembly comprising:
a plurality of electrical paths configured to electrically couple analog output signals from one of said imaging sensor arrays to two or more of said integrated circuits; and
a first analog bus configured to electrically couple analog output signals from a first said sensor array quadrant to a first group of four said integrated circuits.

11. The sensor assembly of claim 10 wherein said interconnect assembly further comprises a second analog bus configured to electrically couple analog output signals from a second said sensor array quadrant to a second group of four said integrated circuits.

12. The sensor assembly of claim 11 wherein said interconnect assembly further comprises a third analog bus configured to electrically couple analog output signals from a third said sensor array quadrant to a third group of four said integrated circuits.

13. The sensor assembly of claim 10 wherein said interconnect assembly is configured to electrically connect: an analog output signal from a sensor in a first column and first row of said two dimensional array of sensors to a first of said integrated circuits, an analog output signal from a sensor in a fifth column and said first row to said first integrated circuit, and an analog output signal from a sensor in a third column and a second row to said first integrated circuit.

14. The sensor assembly of claim 10 wherein said interconnect assembly further comprises one of gold-plated lands and solder balls on a printed circuit board for electrically coupling to said plurality of imaging sensor arrays.

15. The sensor assembly of claim 10 wherein said sensor signal processing components comprise one of a preamplifier and an analog-to-digital converter.

16. A computed tomography imaging system comprising:
an x-ray source mounted in a gantry, said x-ray source rotatable about an imaging target;
a detector assembly for receiving x-ray emission from said x-ray source, said detector assembly including:
a plurality of imaging sensor arrays electrically coupled to a sensor substrate;
a plurality of integrated circuits electrically coupled to a package substrate;
an interconnect assembly electrically disposed between said sensor substrate and said package substrate, said interconnect assembly comprising:
a first electrical path configured to electrically couple analog output signals from a first sensor in a first of said imaging sensor arrays to a first of said integrated circuits;
a second electrical path configured to electrically couple analog output signals from a second sensor to a second of said integrated circuits, said first sensor being disposed adjacent to said second sensor; and
a third electrical path configured to electrically couple analog output signals from a third sensor in said first imaging sensor array to said first integrated circuit, said second sensor being disposed between said first sensor and said third sensor;
an imager control system for selectively modulating said x-ray source; and
a computer for receiving data from said detector assembly.

17. The computed tomography imaging system of claim 16 wherein said interconnect assembly forms a unitary component with said package substrate.

18. The computed tomography imaging system of claim 16 wherein said package substrate further comprises a plurality of power lines, each said power line connected to a respective one of said integrated circuits.

19. The computed tomography imaging system of claim 16 wherein at least one of said plurality of integrated circuits comprises one of a preamplifier and an analog-to-digital converter.

20. A computed tomography imaging system of claim 16 comprising means to recover and/or correct imaging data output when one of said sensors fails, said means comprising an electrical interconnection pattern or an algorithm.

* * * * *